US010792257B2

(12) United States Patent
Moretto et al.

(10) Patent No.: US 10,792,257 B2
(45) Date of Patent: Oct. 6, 2020

(54) PHARMACEUTICAL COMPOSITIONS COMPRISING SAFINAMIDE

(71) Applicant: Zambon S.P.A., Bresso (Milan) (IT)

(72) Inventors: Alberto Moretto, Ponte San Nicolo' (IT); Alessandra De Lazzari, Padua (IT); Deborah Teoli, Vicenza (IT)

(73) Assignee: Zambon S.P.A., Bresso (Milan) (IT)

( * ) Notice: Subject to any disclaimer, the term of this patent is extended or adjusted under 35 U.S.C. 154(b) by 0 days.

(21) Appl. No.: 16/305,115

(22) PCT Filed: May 30, 2017

(86) PCT No.: PCT/EP2017/063063

§ 371 (c)(1),
(2) Date: Nov. 28, 2018

(87) PCT Pub. No.: WO2017/207587

PCT Pub. Date: Dec. 7, 2017

(65) Prior Publication Data

US 2020/0085769 A1 Mar. 19, 2020

(30) Foreign Application Priority Data

May 31, 2016 (IT) ........................ 102016000056247

(51) Int. Cl.

| | |
|---|---|
| ***A61K 31/165*** | (2006.01) |
| ***A61K 9/00*** | (2006.01) |
| ***A61K 9/50*** | (2006.01) |

(52) U.S. Cl.
CPC .......... *A61K 31/165* (2013.01); *A61K 9/0056* (2013.01); *A61K 9/5026* (2013.01); *A61K 9/5047* (2013.01)

(58) Field of Classification Search
None
See application file for complete search history.

(56) References Cited

U.S. PATENT DOCUMENTS 5,082,669 A * 1/1992 Shirai .................. A61K 9/5047
424/461

FOREIGN PATENT DOCUMENTS

| | | | |
|---|---|---|---|
| CN | 104546747 | A | 4/2015 |
| WO | 2003041683 | A2 | 5/2003 |
| WO | 2008119033 | A1 | 10/2008 |
| WO | 2011085188 | A1 | 7/2011 |
| WO | 2011098456 | A1 | 8/2011 |

OTHER PUBLICATIONS

International Search Report and Written Opinion of Counterpart PCT/EP2017/063063 dated Sep. 1, 2017.

* cited by examiner

*Primary Examiner* — Aradhana Sasan
(74) *Attorney, Agent, or Firm* — Silvia Salvadori, P.C.; Silvia Salvadori

(57) ABSTRACT

The present invention relates to pharmaceutical compositions comprising safinamide, and, more particularly, to taste-masked particles comprising said active ingredient or pharmaceutically acceptable salts thereof, oral dosage forms that include said particles and a process for preparing them.

20 Claims, No Drawings

PHARMACEUTICAL COMPOSITIONS COMPRISING SAFINAMIDE

This application is a U.S. national stage of PCT/EP2017/063063 filed on 30 May 2017, which claims priority to and the benefit of Italian Application No. 102016000056247 filed on 31 May 2016, the contents of which are incorporated herein by reference in their entireties.

The present invention relates to pharmaceutical compositions comprising safinamide, and, more particularly, to taste-masked particles comprising said active ingredient or pharmaceutically acceptable salts thereof, oral dosage forms that include said particles and a process for preparing them.

Safinamide (2 S)-2-[[4-[(3-fluorophenypmethoxy]phenyl]methyl amino]propanamide, of formula

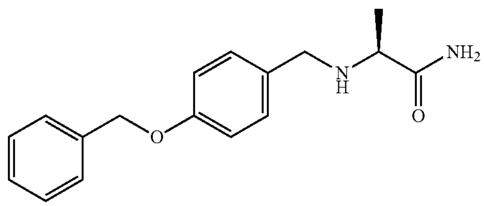 [SMILES: C[C@H](NCc1ccc(OCc2ccccc2)cc1)C(N)=O]

is a highly selective and reversible MAO-B inhibitor that causes an increase in the extracellular levels of dopamine in the striatum. Safinamide is associated with state-dependent inhibition of the voltage dependent sodium channels (Na+) and modulation of the stimulated release of glutamate.

Safinamide methanesulfonate is the active ingredient of an EMA-approved drug (Xadago®) that is administered in the form of oral tablets.

Xadago® is indicated for the treatment of adult patients with idiopathic Parkinson's disease as add-on therapy at a stable dose of levodopa (L-dopa) alone or in combination with other drugs for Parkinson's disease in mid- to late-stage fluctuating patients; safinamide acts by a mechanism of action that is both dopaminergic and non-dopaminergic.

Safinamide methanesulfonate film-coated oral tablets to be swallowed, at a dosage of 50 and 100 mg, are currently on the market.

These tablets are characterized by an immediate release profile.

As these tablets are to be swallowed, it is required that patients in therapy should be able to perform the action of swallowing correctly.

However, swallowing may prove difficult for some categories of patients, for example, for elderly patients or for patients who barely cooperate with paramedical personnel, in particular, because of progression of disabling pathologies such as Parkinson's disease.

In these clinical situations the patient has difficulty in coordinating the movements necessary for swallowing, which require closure of the glottis and simultaneous contraction of the muscles of the larynx, which have to propel the whole tablet into the oesophagus.

In these cases it would be advisable to replace the tablets that are to be swallowed with water with other oral dosage forms in which swallowing is made easier. Patent EP1613296 (Newron Pharmaceuticals S.p.A.) describes novel compositions and methods for treating Parkinson's disease and, specifically, methods for treating Parkinson's disease by administering safinamide in combination with levodopa. This patent describes generic pharmaceutical formulations that comprise the active ingredient, inter alia, formulations for oral administration such as tablets, capsules, elixirs, syrups and oral suspensions.

The marketing authorization document, issued by the EMA, relating to Xadago® describes a film-coated tablet of 7 mm diameter, round, biconcave, orange to copper in colour, with metallic gloss, embossed with the dose "50" mg on one side (or 100 mg, with different colour), the qualitative composition of which is given below in Table 1:

TABLE 1

| Table core | Film coating |
|---|---|
| Safinamide methanesulfonate | Hypromellose |
| Microcrystalline cellulose | Polyethylene glycol 6000 |
| Type A crospovidone | Titanium dioxide (E171) |
| Magnesium stearate | Red iron oxide (E172) |
| Colloidal anhydrous silica | Mica (E555) |

The production process envisages dry compaction of the active ingredient mixed with excipients (internal phase), mixing of the compacted material with further excipients (external phase), compression of the final mixture into tablets and coating the latter with coloured polymer film.

Chinese patent application CN 104546747 (Xiamen Meijisi Pharmaceutical Co., Ltd.) describes. a pharmaceutical composition comprising safinamide methane sulfonate with an alleged satisfactory dissolution profile obtained by modulating the proportions of the excipients and, mainly, by controlling the particle size of the active ingredient, which is micronized (D90: 5-50 μm); in general terms, said composition comprises safinamide mesylate as well as a hydrophilic diluent, a water-soluble polymeric binder, a disintegrarit, flavouring and a lubricant, in which the active ingredient is contained at a percentage of about 20-30 wt %.

In particular, Example 5 describes an orodispersible tablet that contains 50 mg of safinamide methanesulfonate, the qualitative and quantitative composition of which is given in the following Table 2:

TABLE 2

| Tablet core | % |
|---|---|
| Safinamide methanesulfonate | 20.0 |
| Mannitol | 50.5 |
| Microcrystalline cellulose | 20.0 |
| Low-sub. Hydroxypropylcellulose | 8.0 |
| Hydroxypropylmethylcellulose | 0.5 |
| Magnesium stearate | 1.0 |
| Total | 100.0 |

As described above, in particular clinical situations such as Parkinson's disease, for which Xadago® is indicated, it would be advisable to replace tablets that are to be swallowed with water with other oral dosage forms in which swallowing is made easier.

These oral forms facilitate swallowing for the patient, but they have a potential technical problem in that they may allow direct contact between the molecule of the active ingredient and the taste buds of the patient's tongue and other receptors of the oral cavity that contribute to the total effect of palatability.

For this reason, they must be formulated and produced in such a way that the patient does not perceive the taste of the active ingredient and other possible sensory effects, for example, irritation of the oral mucosa; some pharmaceutical molecules are, in fact, characterized by a very unpleasant taste and in worse cases also by effects of irritation of the tongue and palate.

To the inventors' best knowledge, it does not appear that the problem associated with the organoleptic characteristics of the active ingredient safinamide or a pharmaceutically acceptable salt thereof has ever been disclosed in the prior art.

In particular, the aforementioned patent application CN 104546747 gives examples of the preparation of orodispersible tablets, which are therefore easier to swallow, by a process of wet granulation followed by compression, in which there does not appear to be any attempt to modify the organoleptic, characteristics of the active ingredient.

The present inventors note that safinamide in the form of free base and/or of a pharmaceutically acceptable salt thereof, in particular safinamide methanesulfonate, is a molecule that is characterized by an unpleasant taste, with a bitter component that is decidedly very intense, astringent and moreover with a pronounced tendency to irritate the mucosae of the first section of the oropharynx.

In order to avoid that the patient refuses the treatment with safinamide, it is essential to completely mask the taste of the active ingredient during administration. Formulating a tablet with rapid disintegration in the oral cavity without masking the taste of safinamide would lead to full perception of the taste of the active ingredient by the patient with loss of acceptability of the dosage form and adherence to the treatment, with consequent worsening of the clinical picture.

In addition to the known difficulties of a technological nature, the unsuitable organoleptic characteristics of some active pharmaceutical ingredients constitute one of the main problems that are encountered when trying to supply oral dosage forms that are easier to swallow.

The techniques that are generally used in. an attempt to guarantee effective taste-masking include various processes of a chemical and physical. nature, which must necessarily take into account the characteristics of the, specific active ingredient as well as the peculiarities of the dosage form adopted.

In fact, a person skilled in the art is well aware of the limitations in the area of formulation that are dictated by the intrinsic organoleptic properties, dimensions, shape, particle size distribution and solubility of the active ingredient that will be incorporated in the selected dosage form.

In order to face these unfavourable organoleptic characteristics, the common formulation practice, known by experts in this field, envisages including flavourings and sweeteners in the formulation so as to mask the unpleasant notes of the active ingredients.

Moreover, it is known in the prior art that it is possible to reduce or even completely eliminate the irritant effect of some active ingredients by suitably varying the pH of the pharmaceutical preparation.

Patent EP 2594266 in the name of the same applicant describes how suitable modification of pH is able to eliminate the irritant effect of ibuprofen or of pharmaceutically acceptable salts thereof.

In the specific case of safinamide methanesulfonate, the practice of using sweeteners and flavourings, even suitably combined, did not provide effective masking of its sensory characteristics; moreover, attempts to modify the pH of the pharmaceutical preparation did not lead to a reduction of the irritant effect in the oral cavity.

This result is penalizing for the patient when safinamide methanesulfonate is included in oral dosage forms for easier swallowing, because it would compel the patient to perceive the unpleasant taste and irritant effect of the active ingredient in the oral cavity.

This difficulty of masking the taste of safinamide methanesulfonate is due, firstly, to the fact that safinamide has a bitter component that is decidedly very intense combined with an equally intense tendency to irritate the tongue and palate; moreover, being safinamide methanesulfonate an active ingredient fairly soluble in saliva, the patient's perception of the taste is immediate.

Often pharmaceutical molecules that are very bitter actually have low solubility in saliva and perception is not instant as in the case of safinamide.

Alternative taste-masking techniques envisage the use of physical barriers between the active ingredient and the oral mucosa (colloidal systems of high viscosity), reduction of its solubility by modifying, for example, the pH of the pharmaceutical preparation or through encapsulation techniques (granulation, coating, micro-encapsulation, etc.); moreover, a person skilled in the art knows other ways of masking taste that are based on chemical interaction of the active principle with molecules capable of interacting strongly with it, called ion-exchange resins, or the creation of reversible complexes between molecules of active principles and molecules with a cyclic polyol character (cyclodextrins).

However, many of the aforementioned approaches involve more or less significant chemical and/or physical modifications of the pharmaceutically active ingredient, which will influence the stability, the dosage form and, first of all, its onset of action and bioavailability.

Although various techniques are known for preparing dosage forms for easier swallowing, it has become necessary to investigate innovative methods that make it possible to formulate pharmaceutical compositions comprising safinamide or a pharmaceutically acceptable salt thereof capable of disintegrating rapidly in the oral cavity with excellent organoleptic properties and that are able to release the active ingredient in the gastrointestinal tract with kinetics equivalent to the dosage form currently on the market.

The present inventors found, unexpectedly, that by converting safinamide or a pharmaceutically acceptable salt thereof, in particular safinamide methanesulfonate, into a plurality of solid particles through an agglomeration process and by applying a polymeric coating composition on every particle, the drawbacks of the prior art are overcome.

During administration of the oral pharmaceutical preparation for easier swallowing, said particles that form the subject matter of the present invention are able to pass through the patient's oral cavity and avoid perception of the unpleasant organoleptic characteristics of safinamide or a pharmaceutically acceptable salt thereof and, owing to this important result, allow patients with difficulty swallowing to derive the full benefit from the drug treatment.

Therefore, the present invention is directed to pharmaceutical compositions and production processes thereof in which safinamide or a pharmaceutically acceptable salt thereof, preferably safinamide methanesulfonate, is incorporated in oral dosage forms for easier swallowing such as, for example, tablets that disintegrate rapidly in the oral cavity, orodispersible films, chewable tablets, orodispersible microtablets, orodispersible powders, effervescent tablets, water-dispersible tablets, water-dispersible powders, and the like; in these preparations, safinamide or a pharmaceutically acceptable salt thereof is present in a form such as to guarantee complete masking of the very unfavourable organoleptic characteristics of the active ingredient without compromising the kinetic release profile in the gastrointestinal tract.

Therefore, the present invention relates to a plurality of particles each of which including:

a. a core comprising safinamide or a. pharmaceutically acceptable salt thereof and a binder;

b. a polymer composition which forms a coating on said core.

The particles according to the present invention consist substantially of a core comprising the active ingredient on which a polymer composition able to mask the organoleptic characteristics of the latter is suitably applied.

Generally said particles have moderate dimensions not more than 500 μm, for the purpose of avoiding disagreeable sensory perceptions once introduced into the oral cavity as such or as part of the selected pharmaceutical dosage form.

The core according to the invention comprises safinamide or a pharmaceutically acceptable salt thereof, a binder and optionally one or more pharmaceutical excipients and is prepared, in general terms, by common agglomeration techniques to give granules, beads, pearls, spheroids, pellets, and the like.

Said core generally consists of agglomerates with dimensions in the range 150-500 μm, preferably not polydisperse; preferably, according to the invention said agglomerates have a particle size in the range 200-450 μm.

Safinamide is preferably used in crystalline solid form having an average particle size in the range 5-50 μm.

Pharmaceutically acceptable salts of safinamide according to the present invention include addition salts with inorganic acids, for example nitric, hydrochloric, sulphuric, perchloric and phosphoric acid or with organic acids, for example acetic, propionic, glycolic, lactic, oxalic, malonic, malic, tartaric, citric, benzoic, cinnamic, mandelic, methanesulphonic and salicylic acid, safinamide methanesulfonate being the preferred salt.

Preferably, the particles formulated and produced according to the invention comprise from 10 to 80 wt % of safinamide base, more preferably from 20 to 60 wt % of safinamide or an equivalent dose of a salt thereof.

Preferably, the dosage forms comprising the particles formulated and produced according to the invention include a dose of safinamide base of 50 or 100 mg or an equivalent dose of a salt thereof.

The term binder according to the invention means a pharmaceutical excipient such as, for example, hydroxypropylcellulose (HPC), hydroxypropylmethylcellulose (HPMC), microcrystalline cellulose, polyethylene glycol (PEG), methylcellulose (MC), povidone (PVP), polyethylene oxide (PEO), polyvinyl alcohol (PVA), modified starches and others, alone or in combination.

Preferred binders according to the invention are selected from povidone (PVP), polyethylene glycol (PEG), pregelatinized starch, hydroxypropylmethylcellulose (HPMC) and microcrystalline cellulose.

Pharmaceutically acceptable excipients that may optionally be present in the core of the particles according to the present invention comprise: diluents, for example microcrystalline cellulose (MCC), lactose, anhydrous or monohydrate, pregelatinized starch, mannitol, isomalt, sorbitol and similar carbohydrates, dicalcium phosphate, anhydrous or dihydrate, maltodextrins and others; disintegrants, for example: crospovidone, sodium croscarmellose, sodium starch glycolate, partially pregelatinized starch and others; and glidants, for example: colloidal silica, talc and others.

These optional excipients of the particles according to the present invention are included in the core at a percentage preferably in the range 0-10 wt %; even more preferably in the range 0-5 wt %.

In a preferred aspect, the core of the particles according to the present invention comprises one or more binders and one or more glidants.

The core of the particles according to the present invention preferably comprises a binder alone or in admixture at a percentage in the range 0.5-60 wt %; more preferably in the range 2.0-50 wt %; even more preferably in the range 2.0-30 wt %. In another preferred aspect, the core of the particles according to the present invention is characterized by a bulk density in the range 0.15-0.70 g/ml, of rounded shape with a smooth surface; even more preferably with a bulk density in the range 0.20-0.50 g/ml.

The polymer composition that forms a coating on said core according to the invention may comprise a water-soluble polymer, a water-insoluble polymer or a mixture thereof.

Suitable polymers according to the invention are polymers with pH-dependent water solubility and water-soluble and water-insoluble celluloses such as, for example, basic polymethacrylate butylate, ethylcellulose alone or mixed with hydroxypropylmethylcellulose and ethylcellulose mixed with basic polymethacrylate butylate.

Said polymer compositions may be used directly as powders, as aqueous dispersions or in the form of solutions in suitable organic solvents.

Some commercially available compositions that may be the object of the present invention include copolymers of methacrylic acid and celluloses available with the trademark Eudragit L100, Eudragit S100, Eudragit L30D, Eudragit E100, Eudragit EPO (Evonik), Kollicoat Smartseal 30 D, Kollicoat IR, Kollicoat MAE 30D, Aquacoat ECD, Aquacoat ARC, Aquacoat CPD (FMC), Surelease (Colorcon) and the like.

Said coating polymer compositions may moreover include one or more functional excipients for coating selected from plasticizers, glidants, antiaggregants and release regulators (pore formers).

The content of the polymeric coating composition is generally in the range 10-70 wt % and preferably in the range 20-40 wt %.

In a preferred aspect of the invention the particles according to the invention have a qualitative and quantitative composition given below in Table 3:

TABLE 3

| Component | % |
|---|---|
| Core | 30-90 |
| Polymer composition | 10-70 |
| Total | 100 |

In another preferred aspect, the particles according to the present invention are characterized by a bulk density in the range 0.30-0.70 g/ml; even more preferably by a bulk density in the range 0.40-0.60 g/ml.

The particles according to the present invention are prepared by a process which comprises:

a. agglomerating the active pharmaceutical ingredient and the binder to give the core;

b. coating said core with a polymer composition.

Said particles according to the invention are prepared by using known methods of agglomeration and coating, application of which to the specific active ingredient safinamide has proved, owing to its physicochemical peculiarities, to be of a criticality that goes well beyond the routine work of a person skilled in the art. Said particles are, preferably, prepared by mixing the active principle with the binder and, optionally, one or more pharmaceutically acceptable excipients defined above. Said mixture is agglomerated by wet or dry processes by using technologies such as fluidized-bed granulation, high-shear granulation, extrusion, roll compaction etc. to give a core, preferably, in the form of micropellets; said core is dried in the case of wet processes or cooled in the case of melt processes and optionally milled and/or sifted.

The inventors applied the polymer-based coating to the core of the present invention to obtain taste masking of the active principle.

The polymer composition may be applied on the core according to the invention by common coating techniques used in the pharmaceutical industry including, inter alias, fluidized-bed coating, pan coating and spray coating.

For applying the coating polymers, the inventors preferably used fluidized-bed technology that is well known to a person skilled in the art; owing to the vast amount of experimental work carried out, the inventors clearly identified the qualitative-quantitative compositions of the polymeric coating composition to apply to the cores of safinamide or a pharmaceutically acceptable salt thereof to obtain adequate masking of the organoleptic characteristics thereof.

The application of a polymeric coating composition on the cores comprising the active ingredient is a technique that is known by persons skilled in the art.

It is important to note that in the case of safinamide methanesulfonate the oral dosage forms for improved swallowing should desirably have a release profile equivalent to those of tablets to be swallowed that are already being marketed; this release profile is immediate and it is therefore necessary to apply a type of coating film that only lasts a few minutes so that it only exerts its action during oral transit of the drug and disintegrates immediately after swallowing to provide equivalence of the release profile relative to tablets that are to be swallowed.

In one aspect of the invention, mixing of the powders included in the core and their agglomeration as well as coating with the polymer composition take place in the same equipment, preferably, in a fluidized bed.

In this case, first of all the initial mixture of powders is fluidized before being agglomerated by spraying with at least the liquid binder; the core thus obtained is discharged, sifted to recover the granulometric fraction of interest and reloaded in the fluidized bed; the core is coated by spraying with the polymer composition, followed by the drying step.

These particles are preferably suitable for inclusion in all oral forms in which their compression is not envisaged; particles of this type are easily obtained and are characterized by a pseudospherical shape and by excellent flowability.

In a preferred aspect of the invention, the agglomeration step and the step of coating with polymer composition are carried out in different items of equipment.

In this case, the initial mixture of powders is agglomerated with the mixture of excipients comprising at least the binder, for example using a high-shear granulator, an extruder or a roll compactor; the core thus obtained is discharged, calibrated for particle size, introduced into the fluidized bed and then coated by spraying the polymer composition and, finally, dried.

Said particles are preferably suitable for inclusion in all oral dosage forms in which their subsequent compression is envisaged.

It would in fact be desirable for particles of this type to possess particular physical characteristics so that during the compaction process they do not deform and/or fragment, so as not to lose the valuable protection of the coating film; moreover, to obtain efficient particle coating with taste-masking polymer systems it would also be desirable to use agglomeration techniques capable of creating cores with a particularly smooth surface and with spherical geometry.

The present inventors obtained, surprisingly, this optimum type of particles by applying to safinamide or a pharmaceutically acceptable salt thereof, agglomeration techniques capable of imparting high density to the cores, characterized in addition by a suitable shape for their necessary coating with a taste-masking polymer composition.

Therefore the present invention further relates to a plurality of particles each of which includes:

a. a core comprising safinamide or a pharmaceutically acceptable salt thereof and a binder;

b. a polymer composition that forms a coating on said core;

wherein said core is prepared by melt agglomeration.

According to the present invention, "melt agglomeration" means a dry process, in which a mixture of powders comprising safinamide or a pharmaceutically acceptable salt thereof, at least one binder and optionally other additives as mentioned above, is heated with stirring until the melting point of the binder or binder mixture is reached; and then cooled to room temperature, keeping it stirred, to give the core of the particles according to the present invention.

This melt agglomeration procedure may be carried out using commercially available equipment such as, for example, the high-speed rotary granulator (high-shear mixer) made by the company Zanchetta, model Rotojunior 10 or similar equipment such as Glatt, Collette, Diosna or melting extruders such as Pharma 11 by Thermo. Binders suitable for a melt agglomeration procedure according to the invention are glycerol monostearate, glycerol distearate, carnauba wax, stearic acid, hydrogenated castor oil, polyvinylpyrrolidone (PVP), polylactic-co-glycolic acid (PLGA), polyvinyl alcohol, ethylcellulose, hydroxypropylmethylcellulose (HPMC), polymethacrylates, poloxamers, polyethylene glycol (PEG), polyethylene oxide (PEO) and the like.

Binders that are particularly suitable, as well as preferred, for a melt agglomeration procedure according to the invention are PEG (polyethylene glycol), PEO (polyethylene oxides), PVP (polyvinylpyrrolidone) and PVA (polyvinyl alcohol) used alone or in admixture.

Even more preferred is PEG that is commonly used in the pharmaceutical field; optionally, it is possible to use mixtures of PEGs with different average molecular weight so that the melting point of the mixture is preferably between 40 and 80° C. PEG 3000, PEG 4000, PEG 6000 and PEG 8000, alone or in admixture, are particularly preferred.

In a preferred aspect, the core of the particles according to the present invention is prepared with a binder, alone or in admixure, at a percentage in the range 10-60 wt %; even more preferably in the range 20-40 wt %.

In an even more preferred aspect, the cores of the particles according to the invention have a composition given below in Table 4:

TABLE 4

| Component | % |
|---|---|
| Safinamide base | 50-80 |
| Binder | 20-40 |
| Additives | 0-10 |
| Total | 100 |

A practical embodiment of the invention envisages that a suitable equipment, preferably a high-shear rotary granulator, is charged with a mixture of powders consisting of safinamide or a pharmaceutically acceptable salt thereof, the binder, preferably PEG and optionally other additives, preferably just the glidant; the powders are mixed inside said equipment for some minutes at room temperature; the mixture is then heated with stirring up to the melting point of the binder, preferably about 40-80° C.; the mixture is then cooled to room temperature, keeping it stirred, discharging the cores thus obtained and proceeding to selection of particle size, preferably within the range 200-450 μm, by sifting.

From the technological viewpoint, the aforementioned melt agglomeration procedure guarantees the formation of cores with a high density and regular shape that are particularly suitable for the next steps of coating and optional compaction.

Moreover, the aforementioned melt agglomeration procedure proved to be surprisingly useful for preserving the crystalline structure and stability of the active ingredient safinamide methanesulfonate against the components of the polymeric coating composition.

It is important to note that the aforementioned characteristics of the particles according to the present invention, i.e. a compact core and an effective taste-masking coating suitably formulated, were shown to be perfectly compatible with the desired dissolution profile.

As described above, the particles according to the present invention may then be used as such in pharmaceutical dosage forms for easier swallowing such as, for example, orodispersible or water-dispersible sachets.

Preferably, the particles according to the present invention are incorporated as such or optionally in the presence of suitable pharmaceutically acceptable excipients in dosage forms for easier swallowing such as orodispersible sachets.

Alternatively, the particles according to the present invention may be incorporated in more complex dosage forms for easier swallowing with rapid disintegration, for example tablets that disintegrate rapidly in the oral cavity (ODTs), chewable tablets, orodispersible microtablets, water-dispersible effervescent tablets and orodispersible films.

Therefore the present invention further relates to the use of a plurality of particles as described above in the preparation of an oral dosage form.

Preferred dosage forms according to the present invention are orally disintegrating tablets.

Therefore, in a practical embodiment of the invention safinamide or, a pharmaceutically acceptable salt thereof is agglomerated with at least one binder solution by a wet process or preferably by a dry melt process; the core thus obtained is then coated with a suitable polymer composition; and the particles according to the present invention are then mixed with suitable excipients and converted into rapidly disintegrating tablets that have taste-masking properties even after a prolonged storage time.

Therefore the present invention further relates to the use of the taste-masked particles obtained as described above in the preparation of rapidly disintegrating tablets. Said particles possess good properties of resistance to compaction and flowability and may be used directly in the preparation of oral dosage forms, optionally following mixing with suitable pharmaceutical excipients.

Extraparticulate excipients that may be contained in the dosage forms according to the invention are diluents, for example mannitol, lactose, isomalt, sorbitol, xylitol and the like; optionally binders, for example microcrystalline cellulose, ethylcellulose; hydroxypropylcellulose, polyvinylpyrrolidone, polyethylene glycol, lactose, dicalcium phosphate and combinations thereof; optionally disintegrants, for example crospovidone, sodium starch glycolate, croscarmellose and the like; optionally lubricants, for example magnesium stearate, sodium stearyl fumarate, polyethylene glycol, sodium benzoate and the like.

In a preferred aspect of the invention the diluents are selected from mannitol, isomalt, sorbitol, xylitol and maltodextrins; the binders are selected from microcrystalline cellulose, lactose, polyvinylpyrrolidone and polyethylene glycol; the disintegrants are selected from crospovidone, sodium starch glycolate and croscannellose; the lubricants are selected from magnesium stearate, sodium stearyl fumarate and polyethylene glycol.

In a preferred aspect of the present invention the rapidly disintegrating tablets according to the invention have a qualitative and quantitative composition given below in Table 5:

TABLE 5

| Component | % |
|---|---|
| particles | 30-70 |
| diluent | 20-70 |
| binder | 5-20 |
| disintegrant | 2-30 |
| lubricant | 1-5 |
| Total | 100 |

As described above, in particular clinical situations such as Parkinson's disease for which Xadago® is indicated, it would be appropriate to replace tablets that are to be swallowed with water with other oral dosage forms in which swallowing is made easier.

To the inventors' best knowledge, it appears that the problem associated with the organoleptic characteristics of the active ingredient safinamide or a pharmaceutically acceptable salt thereof has never been identified in the prior art, although patent application CN 104546747 cited above describes the preparation of orodispersible tablets.

The present invention makes it possible to prepare particles comprising safinamide or a pharmaceutically acceptable salt thereof and to formulate pharmaceutical compositions capable of disintegrating rapidly in the oral cavity with excellent organoleptic properties and that are able to release the active ingredient in the gastrointestinal tract with kinetics equivalent to so-called immediate release. There are many drawbacks facing a person skilled in the art when formulating orodispersible dosage forms, especially when said forms are to incorporate active pharmaceutical ingredients that possess unfavourable physicochemical and/or organoleptic properties.

To date, there is no universal technology in the art suitable for applying to any active ingredient whatever.

In particular, taste-masking techniques must satisfy a number of criteria connected with the preparation process and, mainly, with the specific product; stability of the active ingredient, particle size and shape, mechanical and physical characteristics as well as the qualitative and quantitative composition of the polymeric coating composition are just some of the countless variables that have to be taken into account and managed in the formulation approach.

By using the plurality of solid particles described in the present invention, it is possible to prepare oral dosage forms for easier swallowing which, when the patient takes the drug, guarantee total masking of the unpleasant sensory profile of safinamide or a pharmaceutically acceptable salt thereof, preferably safinamide methanesulfonate, without altering its desired dissolution profile.

It is therefore clear that the composition according to the present invention is advantageous compared to those already described in the literature.

For this purpose, the tablets according to the present invention have physical characteristics that satisfy the requirements of the Official Pharmacopoeias.

For example, the hardness of the tablets is between 2.0 and 5.0 kP, the friability is below 1% and the disintegration time is less than 1 minute.

Moreover, the tablets claimed in this document have dissolution characteristics in vitro comparable to those of the immediate-release tablets currently marketed. The kinetic properties of immediate release in the stomach of the particles according to the present invention and of the rapidly disintegrating tablets comprising said particles, were evaluated by determining the percentage release of the active ingredient when tested for dissolution of the dosage form in simulated gastric fluid or 0.1N hydrochloric acid; release exceeding 80% of the dose in about 30 minutes is to be regarded as satisfactory.

Finally, the taste-masking properties of the particles according to the present invention and of rapidly disintegrating tablets comprising said particles were evaluated by determining the percentage release of the active ingredient when tested for dissolution of the dosage form in simulated saliva at a pH of about 6.8; release of not more than 10% of the dose in 1 minute is to be regarded as satisfactory.

For the purpose of better illustrating the present invention, the following non-limiting examples are now given.

EXAMPLE 1

Preparation of the Cores: Wet Agglomeration a Fluidized Bed (Top Spray Insert):

Safinamide methanesulfonate and silicon dioxide were mixed in a Cyclops lab (Zanchetta) rotating-body mixer for 20 minutes. The binder solution consisting of demineralized water and dissolved or dispersed binder was prepared separately. The mixture of powder was then introduced into the Ghibli Lab (IMA) fluidized bed and was fluidized at an air flow rate of 60-80 $m^3/h$ at a temperature of 60-70° C. Next, the binder solution was sprayed onto the bed of fluidized powder at a flow rate of 20-30 g/min, taking care to maintain the temperature of the product at 28-30° C. On completion of the granulating step, the granules were then dried, maintaining the fluidized powder at a temperature of about 40° C. On completion of the drying step, the product was discharged and sifted, taking care to recover the fraction in the range 200-450 μm.

Using the procedure described above, cores were prepared having the following composition:

Core 1

| | |
|---|---|
| Safinamide methanesulfonate | 93.0% |
| Hydrated precipitated silica | 2.0% |
| PVP K30 | 5.0% |

Core 2

| | |
|---|---|
| Safinamide methanesulfonate | 91.0% |
| Hydrated precipitated silica | 2.0% |
| Pregelatinized starch RX 1500 | 7.0% |

Core 3

| | |
|---|---|
| Safinamide methanesulfonate | 90.0% |
| Hydrated precipitated silica | 2.0% |
| PEG 6000 | 5.0% |

b Rotary Granulator:

Safinamide methanesulfonate and silicon dioxide were mixed in a Cyclops lab (Zanchetta) rotating-body mixer for 20 minutes; the granulating solution was prepared at the same time by dissolving or dispersing the binder in demineralized water. The mixed powder was then put in a Roto Junior 10 (Zanchetta) rotary granulator at paddle speed of about 300 rpm. Then the binder solution sprayer was switched on at a flow rate of 40 ml/min. At the end of the spraying step, the paddle speed was reduced to about 20 rpm and the drying step was started, applying vacuum and raising the product temperature to about 27° C. At the end of the drying step, the product was discharged and sifted recovering the granulometric fraction in the range 200-450 μm.

Using the procedure described above, cores were prepared having the following composition:

Core 4

| | |
|---|---|
| Safinamide methanesulfonate | 94.0% |
| Hydrated precipitated silica | 2.0% |
| PVP K90 | 4.0% |

Core 5

| | |
|---|---|
| Safinamide methanesulfonate | 93.0% |
| Hydrated precipitated silica | 2.0% |
| Hydroxypropylmethylcellulose | 5.0% |

Core 6

| | |
|---|---|
| Safinamide methanesulfonate | 90.0% |
| Hydrated precipitated silica | 2.0% |
| PEG 6000 | 5.0% |

c Extrusion:

Safinamide methanesulfonate and silicon dioxide were mixed in a Cyclops lab (Zanchetta) rotating-body mixer for 20 minutes; the granulating solution was prepared at the same time by dissolving or dispersing the binder in demineralized water. The powder obtained was transferred and mixed in a Roto Junior 10 (Zanchetta) rotary granulator at a paddle speed of about 120 rpm. Then the binder solution sprayer was switched on at a flow rate of 180 g/min. At the end of the spraying step, the wet mass was loaded into an extruder, Extruder 20 (Caleva) and extruded at a rate of 500 g/h. The extruded mass was then dried in a stove at about 40° C. and then loaded into a spheronizer, Spheronizer MBS 250 (Caleva) and processed at a speed of about 1500 rpm until the desired granulometric fraction was obtained. At the end of processing, the mass produced was sifted, recovering the granulometric fraction in the range 200-450 μm.

Using the procedure described above, cores were prepared having the following composition:

Core 7

| | |
|---|---|
| Safinamide methanesulfonate | 91.0% |
| Hydrated precipitated silica | 2.0% |
| Microcrystalline cellulose | 7.0% |

Core 8

| | |
|---|---|
| Safinamide methanesulfonate | 93.0% |
| Hydrated precipitated silica | 2.0% |
| PVP K30 | 5.0% |

Core 9

| | |
|---|---|
| Safinamide methanesulfonate | 90.0% |
| Hydrated precipitated silica | 2.0% |
| Pregelatinized starch | 8.0% |

EXAMPLE 2

Preparation of the Cores: Dry Agglomeration a Fluidized Bed (Rotor):

Safinamide methanesulfonate and silicon dioxide were mixed in a Cyclops lab (Zanchetta) rotating-body mixer for 20 minutes; then they were put in a fluidized bed, GPCG 1.1 (Glatt), equipped with a rotor insert. The agglomerating agent was added to the mass and the rotor insert was switched on at 350 rpm in an air stream of about 50 $m^3$/h. When the product temperature reached about 55° C., the powder agglomeration step was started. After agglomeration, the powder mass was cooled to about 27° C. employing rotation at 125 rpm and fluidization at an air flow rate of 30 $m^3$/h. On completion of the agglomeration process, the product was discharged and sifting was carried out, recovering the granulometric fraction in the range 200-450 μm.

Using the procedure described above, cores were prepared having the following composition:

Core 10

| | |
|---|---|
| Safinamide methanesulfonate | 90.0% |
| Hydrated precipitated silica | 2.0% |
| PEG 6000 | 8.0% |

Core 11

| | |
|---|---|
| Safinamide methanesulfonate | 90.0% |
| Hydrated precipitated silica | 2.0% |
| Poloxamer 237 | 6.0% |

Core 12

| | |
|---|---|
| Safinamide methanesulfonate | 90.0% |
| Hydrated precipitated silica | 2.0% |
| PEG 4000/PEG 8000 | 8.0% |

b Granulator:

Safinamide methanesulfonate and silicon dioxide were mixed in a Cyclops lab (Zanchetta) rotating-body mixer for 20 minutes; the mixed powder was put in a rotary granulator, Rotocube 60 (IMA), to which the granulating agent in the form of powder was added. The new mass was mixed, operating the paddle at 100 rpm for 20 minutes and then the product temperature was raised to about 55° C. On reaching this temperature, the massing step was started and the paddle speed was increased to 200 rpm and maintained for 30 minutes. At the end of the massing step, the cooling step was started, which envisaged lowering the paddle speed to 80 rpm and the product temperature to 25° C. At the end of the cooling step, the powder obtained was sifted, collecting the granulometric fraction in the range 200-450 μm.

Using the procedure described above, cores were prepared having the following composition:

Core 13

| | |
|---|---|
| Safinamide methanesulfonate | 73.0% |
| Hydrated precipitated silica | 2.0% |
| PEG 6000 | 25.0% |

Core 14

| | |
|---|---|
| Safinamide methanesulfonate | 68.0% |
| Hydrated precipitated silica | 2.0% |
| Poloxamer | 30.0% |

Core 15

| | |
|---|---|
| Safinamide methanesulfonate | 70.5% |
| Hydrated precipitated silica | 2.0% |
| PEG 6000 | 27.5% |

c Extruder:

Safinamide methanesulfonate, the binders and the plasticizers were put in an extruder, Pharma 11 (ThermoFisher) and extruded at a rate of about 800 g/h in the temperature range 100-200° C. (depending on the binder). The extruded mass was cooled to 30° C. and then put in a fluidized bed, GPCG 1.1 equipped with a rotor insert with a milled flat and was spheronized at 1300 rpm. The powder mass produced was then sifted, recovering the granulometric fraction between 200 and 450 μm.

Using the procedure described above, cores were prepared having the following composition:

Core 16

| | |
|---|---|
| Safinamide methanesulfonate | 75.0% |
| PVA | 20.0% |
| PEG 4000 | 5.0% |

Core 17

| | |
|---|---|
| Safinamide methanesulfonate | 68.0% |
| PEG 400 | 5.0% |
| PEG 6000 | 27.0% |

Core 18

| | |
|---|---|
| Safinamide methanesulfonate | 71.0% |
| HPMC | 25.0% |
| PEG 4000 | 4.0% |

d Roll Compactor:

Safinamide methanesulfonate and silicon dioxide were mixed in a Cyclops lab (Zanchetta) rotating-body mixer for 20 minutes; then the powder is loaded into a roll compactor, 120 W Pharma (Alexanderwerk) and compacted at a speed and a pressure between the rolls equal to 3 rpm and 200 bar, respectively. The wafer produced by compaction is ground inside the compactor and forced through a mesh equal to 500 µm. The granules produced are discharged from the compactor and sifted in order to recover the granulometric fraction in the range 200-450 µm.

Using the procedure described above, cores were prepared having the following composition:

Core 19

| | |
|---|---|
| Safinamide methanesulfonate | 83.0% |
| Hydrated precipitated silica | 2.0% |
| Microcrystalline cellulose | 15.0% |

Core 20

| | |
|---|---|
| Safinamide methanesulfonate | 86% |
| Hydrated precipitated silica | 2.0% |
| Hydroxypropylcellulose | 12.0% |

Core 21

| | |
|---|---|
| Safinamide methanesulfonate | 88.0% |
| Hydrated precipitated silica | 2.0% |
| PEG 8000 | 10.0% |

EXAMPLE 3

Coating the Cores a Polymeric Coating Composition: pH-Dependent

The agglomerates of safinamide methanesulfonate prepared according to the teaching of Examples 1 and 2 were introduced into a fluidized-bed system (Ghibli Lab; IMA) and coated with a suspension of Eudragit EPO and functional excipients. During the coating step, the temperature of the agglomerates was maintained at about 30-35° C. with a spray flow rate of 4-5 ml/min and an atomization pressure of 2.0 bar. At the end of the deposition step, the agglomerates were dried for about 1 hour inside the fluidized bed at 40° C.

TABLE 6a composition of the cores coated with Eudragit EPO

| Component | wt % |
|---|---|
| Core | 40-70 |
| Polymer composition | 30-60 |
| Total | 100 |

b Polymeric Coating Composition: Celluloses

The agglomerates of safinamide methanesulfonate prepared according to the teaching of Examples 1 and 2 were introduced into a fluidized-bed system (Ghibli Lab; IMA) and coated with a suspension of ethylcellulose (Surelease Clear/Methocel E5). During the coating step the temperature of the agglomerates was maintained at about 44-48° C. with a spray flow rate of 5-7 ml/min and an atomization pressure of 2.0 bar. At the end of the deposition step, the agglomerates were dried for about 1 hour inside the fluidized bed at 40° C.

TABLE 6b composition of the cores coated with ethylcellulose

| Component | wt % |
|---|---|
| Core | 60-80 |
| Polymer composition | 20-40 |
| Total | 100 |

EXAMPLE 4

Following the procedure described in Example 3, the particles according to the present invention having the following composition were prepared:

Particles 1

| | |
|---|---|
| Core 1 | 46.2% |
| Eudragit EPO | 30.6% |
| Sodium lauryl sulphate | 3.1% |
| Stearic acid | 4.8% |
| Talc | 15.3% |

Particles 2

| | |
|---|---|
| Core 7 | 65.0% |
| Eudragit EPO | 20.0% |
| Sodium lauryl sulphate | 2.0% |
| Stearic acid | 4.0% |
| Talc | 9.0% |

Particles 3

| | |
|---|---|
| Core 10 | 70.5% |
| Surelease clear | 26.3% |
| Methocel E5 | 3.2% |

Particles 4

| | |
|---|---|
| Core 13 | 68.8% |
| Eudragit EPO | 17.8% |

-continued

| | |
|---|---|
| Sodium lauryl sulphate | 1.8% |
| Stearic acid | 2.7% |
| Talc | 8.9% |

Particles 5

| | |
|---|---|
| Core 15 | 71.8% |
| Surelease clear | 24.2% |
| Methocel E5 | 4.0% |

EXAMPLE 5

Preparation of Orally Disintegrating Tablets (ODT) Comprising a Plurality of Particles According to the Invention Particles comprising safinamide methanesulfonate prepared according to the teaching of Examples 3-4 and suitable extraparticulate excipients were mixed in a rotating-body mixer (Cyclops Lab; IMA) for 20 minutes; next, a lubricant was introduced into the container of the mixer and the mixture thus obtained was mixed for a further 3 minutes. Said mixture was then put in an automatic rotary tableting machine, EA8 (Ronchi), to give biconvex round tablets. The compression force was set at 10 kN and the rotary speed at 45 rpm.

TABLE 7 composition of the ODT comprising safinamide methanesulfonate

| Component | Quantity (mg) | wt % |
|---|---|---|
| Particles | 150-350 | 30-70 |
| diluent | 100-350 | 20-70 |
| binder | 25-100 | 5-20 |
| disintegrant | 10-150 | 2-30 |
| lubricant | 5-25 | 1-5 |
| Total | 400-500 | 100 |

EXAMPLE 6

Following the procedure described in Example 5, the rapidly disintegrating tablets having the following composition were prepared:

Tablets 1

| | |
|---|---|
| Particles 1 | 51.0% |
| Mannitol | 28.0% |
| Microcrystalline cellulose | 8.5% |
| Crospovidone | 10.0% |
| Magnesium stearate | 2.5% |

Tablets 2

| | |
|---|---|
| Particles 4 | 54.0% |
| Mannitol | 26.2% |
| Microcrystalline cellulose | 6.2% |
| Crospovidone | 11.1% |
| Magnesium stearate | 2.5% |

Tablets 3

| | |
|---|---|
| Particles 5 | 52.1% |
| Mannitol | 27.6% |
| Microcrystalline cellulose | 7.8% |
| Crospovidone | 10.0% |
| Magnesium stearate | 2.5% |

EXAMPLE 7

Preparation of Orodispersible Powders Comprising a Plurality of Particles According to the Invention The particles prepared according to the procedure described in examples 3 and 4 were used for filling sachets, obtaining orosoluble oral dosage forms of safinamide methanesulfonate. The powders were loaded into a rotating-body mixer, Cyclops Lab (IMA), mixed with suitable extraparticulate excipients for 15 minutes and then distributed into sachets with a net weight of powder equal to 1.0 gram.

TABLE 8 composition of the orodispersible powders comprising particles of safinamide

| Component | Quantity (mg) | wt % |
|---|---|---|
| Particles | 100-400 | 10-40 |
| Extraparticulate excipients | 600-900 | 60-90 |
| Total | 1000 | 100 |

EXAMPLE 8

Following the procedure described in Example 7, sachets were prepared having the following compositions:

Orosoluble Powder 1

| | |
|---|---|
| Particles 1 | 30.0% |
| Mannitol | 42.0% |
| Calcium carbonate | 28.0% |

Orosoluble Powder 2

| | |
|---|---|
| Particles 4 | 28.3% |
| Mannitol | 43.0% |
| Calcium carbonate | 28.7% |

Orosoluble Powder 3

| | |
|---|---|
| Particles 5 | 25.0% |
| Mannitol | 45.0% |
| Calcium carbonate | 30.0% |

EXAMPLE 9

Sensory Evaluation of the Orodispersible Tablets Comprising Particles of Safinamide In order to verify the taste-masking effect of the active pharmaceutical ingredient, safinamide methanesulfonate, a test was performed in vivo by using the orodispersible tablets prepared according to the teaching described in Example 6. Sensory evaluation was carried out by recruiting 5 subjects, who were asked to put a tablet in the mouth, to keep it there until there was any perception of the taste, but no longer than one minute, and report the sensation according to the statements in the following scale:

1=no unpleasant taste and no sensation of irritation;
2=bitter note and just perceptible irritation;
3=bitterness and clearly perceptible irritation;
4=bitterness and very intense irritation;
5=extreme bitterness and unbearable irritation.

After keeping the tablet in the oral cavity for one minute, the test participants were asked to rinse the mouth with plenty of drinking water, avoiding swallowing the mass derived from the tablet.

Each evaluation session was carried out in an environment in which the subject is not influenced by the presence of other testers.

The results of the test for evaluating the orodispersible tablets comprising particles of safinamide methanesulfonate according to the invention are given in Table 9.

TABLE 9 sensory evaluation of ODT tablets comprising safinamide

| Subject | Judgment |
|---|---|
| A | 1 |
| B | 1 |
| C | 1 |
| D | 1 |
| E | 1 |

The sensory evaluation test confirms that the unfavourable organoleptic characteristics of the active ingredient were effectively masked, allowing administration of the active pharmaceutical ingredient in the form of orodispersible tablets.

EXAMPLE 10

Sensory Evaluation of the Orodispersible Powders Comprising Particles of Safinamide Methanesulfonate In order to verify the taste-masking effect of the active pharmaceutical ingredient, safinamide methanesulfonate, a test was performed in vivo by using the orodispersible powders prepared according to the teaching described in Example 8. The sensory evaluation was performed by recruiting 5 subjects, who were asked to put 1 gram of orodispersible powder in the mouth, keep it there for 20 seconds (the time required for forming the semisolid mass that can be swallowed) and report the sensation perceived according to the statements of the following scale:

1=no unpleasant taste and no sensation of irritation;
2=bitter note and just perceptible irritation;
3=bitterness and clearly perceptible irritation;
4=bitterness and very intense irritation;
5=extreme bitterness and unbearable irritation.

After keeping the orodispersible powder in the oral cavity for 20 seconds, the test participants were asked to rinse the mouth with plenty of drinking water, avoiding swallowing the mass derived from the powder.

Each evaluation session was carried out in an environment in which the subject is not influenced by the presence of other testers.

The results of the test for evaluating the orodispersible powders comprising particles of safinamide methanesulfonate according to the invention are given in Table 10:

TABLE 10 sensory evaluation of orodispersible powders containing safinamide

| Subject | Judgment |
|---|---|
| A | 1 |
| B | 1 |
| C | 1 |
| D | 1 |
| E | 1 |

The sensory evaluation test confirms that the unfavourable organoleptic characteristics of the active ingredient were effectively masked, allowing administration of the active pharmaceutical ingredient in the form of orodispersible powder.

The invention claimed is:

1. A plurality of particles, each including:

a. a core comprising safinamide or a pharmaceutically acceptable salt thereof and a binder; and b. a polymer composition which forms a coating on said core.

2. A plurality of particles according to claim 1 wherein said core has a particle size between 200-450 μm.

3. A plurality of particles according to claim 1 wherein said core comprises an amount of safinamide base comprised between 20-60% by weight or the salt equivalent thereof.

4. A plurality of particles according to claim 1 wherein said core comprises safinamide methanesulfonate.

5. A plurality of particles according to claim 1 wherein said binder is selected from the group consisting of povidone (PVP), polyethylene glycol (PEG), pregelatinized starch, hydroxypropyl methylcellulose (HPMC) and microcrystalline cellulose or a mixture thereof.

6. A plurality of particles according to claim 5 wherein said core comprises an amount of said binder alone or in a mixture thereof comprised between 2-30% by weight.

7. A plurality of particles according to claim 1 wherein said core further comprises pharmaceutically acceptable excipients selected from the group consisting of diluents, disintegrants and glidants.

8. A plurality of particles according to claim 1 wherein said core is characterized by a bulk density comprised between 0.20-0.50 g/ml.

9. A plurality of particles according to claim 1 wherein said core is prepared by melt agglomeration.

10. A plurality of particles according to claim 1 wherein said polymer composition comprises a polymer with pH-dependent water solubility, a water-soluble or insoluble cellulose polymer and mixtures thereof.

11. A plurality of particles according to claim 10 wherein said polymer is selected from the group consisting of basic butylated poly-methacrylate, ethyl cellulose alone or in admixture with hydroxypropylmethyl cellulose and ethyl cellulose in admixture with basic butylated poly-methacrylate.

12. A plurality of particles according to claim 1 wherein said polymer composition is present in an amount comprised between 20-40% by weight.

13. A plurality of particles according to claim 1 wherein said polymer composition comprises functional excipients selected from the group consisting of plasticizers, glidants, antiaggregants and pore-formers.

14. A plurality of particles according to claim 1 characterized by a bulk density comprised between 0.40-0.60 g/ml.

15. A process for preparing a plurality of particles according to claim 1 which comprises:

a. agglomerating safinamide or a pharmaceutically acceptable salt thereof and the binder to give the core;

b. coating said core with said polymer composition.

16. A process according to claim 15 wherein said core is prepared by melt agglomeration.

17. A process according to claim 15 wherein said binder is polyethylene glycol (PEG).

18. An orally disintegrating tablet comprising a plurality of particles according to claim 1.

19. A method of preparing an oral dosage form comprising the plurality of particles according to claim 1.

20. The method according to claim 19 wherein said oral dosage form comprises an amount of safinamide base of 50 mg or 100 mg or the salt equivalent thereof.

* * * * *